(12) United States Patent
Bergmann et al.

(10) Patent No.: US 9,261,516 B2
(45) Date of Patent: Feb. 16, 2016

(54) DIAGNOSIS AND RISK STRATIFICATION USING NT-PROET-1

(75) Inventors: Andreas Bergmann, Berlin (DE); Joachim Struck, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 1232 days.

(21) Appl. No.: 12/599,197

(22) PCT Filed: May 8, 2008

(86) PCT No.: PCT/DE2008/000781
§ 371 (c)(1),
(2), (4) Date: Jan. 12, 2010

(87) PCT Pub. No.: WO2008/135038
PCT Pub. Date: Nov. 13, 2008

(65) Prior Publication Data
US 2011/0039283 A1   Feb. 17, 2011

(30) Foreign Application Priority Data

May 8, 2007   (DE) .................... 10 2007 021 443

(51) Int. Cl.
*G01N 31/00* (2006.01)
*G01N 33/53* (2006.01)
*G01N 33/74* (2006.01)

(52) U.S. Cl.
CPC ........ *G01N 33/74* (2013.01); *G01N 2333/5754* (2013.01); *G01N 2800/12* (2013.01); *G01N 2800/32* (2013.01)

(58) Field of Classification Search
CPC ............. C07K 14/765; C07K 14/4713; C07K 2319/00; C07K 2319/31; A61K 31/4439; A61K 47/48284; C12N 15/62
See application file for complete search history.

(56) References Cited

U.S. PATENT DOCUMENTS

| 6,756,483 B1 | 6/2004 | Bergmann et al. |
| 2008/0026414 A1 | 1/2008 | Bergmann et al. |
| 2009/0098571 A1 | 4/2009 | Bergmann et al. |

FOREIGN PATENT DOCUMENTS

| EP | 1121600 B1 | 8/2001 |
| EP | 1564558 B1 | 8/2005 |
| WO | WO-00/22439 A2 | 4/2000 |

OTHER PUBLICATIONS

Jain et al. JIACM, 2002, vol. 3, No. 1, pp. 59-64.*
Struck et al. (Peptides, vol. 26, No. 12, 2005, pp. 2482-2486, of record).*
Struck, et al., "Proteolitic processing pattern of the endothelin-1 precursor in vivo", Peptides, vol. 26, No. 12, 2005, pp. 2482-2486.
Papassotiriou Jana, et al., "Immunoluminometric assay for measurement of the C-terminal endothelin-1 precursor fragment in human plasma", Clinical Chemistry, vol. 52, No. 6, Apr. 20, 2006, pp. 1144-1151.
Giaid Adel, et al.; "Expression of endothelin-1 in the lungs of patients with pulmonary hypertension", New England Journal of Medicine, vol. 328, No. 24, 1993, pp. 1732-1739.
Stewart D J, et al., "Increased Plasma Endothelin-1 in Pulmonary Hypertension Marker or Mediator of Disease?", Annals of Internal Medicine, vol. 114, No. 6, 1991, pp. 464-469.
Humbert Marc, et al., "Cellular and molecular pathobiology of pulmonary arterial hypertension", Journal of the American College of Cardiology, vol. 43, No. 12, Suppl. S, Jun. 16, 2004, pp. 13s-24s.

* cited by examiner

*Primary Examiner* — Lisa Cook
(74) *Attorney, Agent, or Firm* — Novak Druce Connolly Bove + Quigg LLP (57) ABSTRACT

The invention relates to a method for the diagnosis and/or risk stratification of cardiac diseases and diseases of the respiratory tract and lungs. According to said method, the free fragment N-terminal proEndothelin (NT-proET-1; AS 18-52 of the pre-proET according to FIG. 1) or fragments and partial peptides thereof is or are determined.

18 Claims, 3 Drawing Sheets

FIG. 1

| | | | | | | | | | | | | | | |
|---|---|---|---|---|---|---|---|---|---|---|---|---|---|---|
| Met | Asp | Tyr | Leu | Leu | Met | Ile | Phe | Ser | Leu | Leu | Phe | Val | Ala | Cys | Gln |

Met Asp Tyr Leu Leu Met Ile Phe Ser Leu Leu Phe Val Ala Cys Gln
1           5                   10              15
Gly Ala Pro Glu Thr Ala Val Leu Gly Ala Glu Leu Ser Ala Val Gly
            20              25              30
Glu Asn Gly Gly Glu Lys Pro Thr Pro Ser Pro Pro Trp Arg Leu Arg
        35              40              45
Arg Ser Lys Arg Cys Ser Cys Ser Ser Leu Met Asp Lys Glu Cys Val
        50              55              60
Tyr Phe Cys His Leu Asp Ile Ile Trp Val Asn Thr Pro Glu His Val
65              70              75              80
Val Pro Tyr Gly Leu Gly Ser Pro Arg Ser Lys Arg Ala Leu Glu Asn
                85              90              95
Leu Leu Pro Thr Lys Ala Thr Asp Arg Glu Asn Arg Cys Gln Cys Ala
            100             105             110
Ser Gln Lys Asp Lys Lys Cys Trp Asn Phe Cys Gln Ala Gly Lys Glu
        115             120             125
Leu Arg Ala Glu Asp Ile Met Glu Lys Asp Trp Asn Asn His Lys Lys
130             135             140
Gly Lys Asp Cys Ser Lys Leu Gly Lys Lys Cys Ile Tyr Gln Gln Leu
145             150             155             160
Val Arg Gly Arg Lys Ile Arg Arg Ser Ser Glu Glu His Leu Arg Gln
                165             170             175
Thr Arg Ser Glu Thr Met Arg Asn Ser Val Lys Ser Ser Phe His Asp
            180             185             190
Pro Lys Leu Lys Gly Lys Pro Ser Arg Glu Arg Tyr Val Thr His Asn
        195             200             205
Arg Ala His Trp
210

1-17 signal peptide 18-52 NT-proET-1

53-73 mature ET-1

53-90 Big-ET-1 (or 74-90)

DIAGNOSIS AND RISK STRATIFICATION USING NT-PROET-1

RELATED APPLICATIONS

This application is a national stage application (under 35 U.S.C. §371) of PCT/DE2008/000781, filed May 8, 2008, which claims benefit of German application 102007021443.1, filed May 8, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 14519_44_US_Seq_Listing. The size of the text file is 4 KB, and the text file was created on Oct. 15, 2010.

The invention relates to a method for the diagnosis and/or risk stratification of heart diseases and diseases of the respiratory tract and lungs, wherein a determination of the free fragment N-terminal proendothelin (NT-proET-1; AS 18-52 of the preproET according to FIG. 1), or fragments and partial peptides thereof, is carried out.

In order to apply a suitable therapy, an early diagnosis and differentiation of heart diseases and/or diseases of the respiratory tract and lungs are necessary already in the emergency room, in conjunction with the need to make clinical decisions. In the state of the art, mature ET-1 (21 AS) is described for diagnostics purposes, including the precursor protein Big-ET1 (38AS, refer to FIG. 1) (Rossi G P, Seccia T M, Albertin G, Pessina A C. Measurement of endothelin: clinical and research use. Ann Clin Biochem 2000; 37(Pt 5): 608-26.2; Aubin P, Le Brun G, Moldovan F, Villette J M, Creminon C, Dumas J, et al. Sandwich-type enzyme immunoassay for big endothelin-I in plasma: concentrations in healthy human subjects unaffected by sex or posture. Clin Chem 1997; 43: 64-70). Furthermore, it is known that endothelin prohormones for the diagnosis of sepsis are disclosed in WO 00/22439 and EP 1121600 B1 by the applicant.

In addition, the C-terminal proendothelin fragments (CT-proET-1) having the amino acid sequences 93-212 or 168-212 of the preproendothelin (FIG. 1, SEQ ID No. 1) for the diagnosis of cardiovascular diseases for the indirect determination of the endothelin-1 or the big-endothelin-1 content are described in EP 1564558 B1. The disadvantage of the known diagnostic methods, using the markers known so far, however, continues to be that an early and comprehensive detection of risk patients is not always sufficiently successful, and risk stratification therefore is not sufficient. An object of the invention is therefore to develop a method for the risk stratification of heart diseases and diseases of the respiratory tract and lungs that enables improved detection of risk patients.

Furthermore it is disadvantageous that in the prior art typically the sensitivity and/or specificity of the markers is insufficient.

Another object is therefore to provide a method for the risk stratification of heart diseases and diseases of the respiratory tracts and lungs, wherein at least one marker, or a combination of markers, has sufficient sensitivity and specificity in an in-vitro diagnosis.

It is therefore the object of the present invention to provide a method for the diagnosis and/or risk stratification of heart diseases and/or diseases of the respiratory tracts and lungs.

The object is achieved by a method for the diagnosis and risk stratification of heart diseases and diseases of the respiratory tract and lungs, wherein a determination of the N-terminal proendothelin (in short: "NT-proET-1"), or fragments and partial peptides thereof, is carried out (hereafter the method according to the invention).

Surprisingly, NT-proET-1, or fragments and partial peptides thereof, exhibit a high sensitivity and specificity for the diagnosis of heart diseases and diseases of the respiratory tract and lungs (refer to examples and figures).

The term "heart diseases" according to the invention in particular includes the "acute coronary syndrome" and the different phases thereof of coronary heart disease, which are immediately life-threatening. This applies in particular to emergency medicine, and specifically to acute myocardial infarction and/or angina pectoris and also sudden cardiac death. In addition to acute myocardial infarction, which according to WHO criteria (WHO (1979): Nomenclature and criteria for diagnosis of ischemic heart disease. Report of the Joint International Society and Federation of Cardiology/World Health Organization task force on standardization of clinical nomenclature, Circulation 59 (3): 607-609) is defined as an acute chest pain event lasting for more than 20 minutes, associated with changes in the ST segment elevation, and/or an increase in myocardial enzymes, the term unstable angina pectoris (AP) was coined, which according to the invention is to be considered part of "heart diseases" (Hamm C W: Leitlinien: Akutes Koronarsyndrom (ACS)-Teil 1: ACS ohne persistierende S-T-Hebung [Guidelines: Acute Coronary Syndrome (ACS)—Part 1: ACS without persistent ST segment elevation]. Z Kardiol (2004) 93:72-90).

As part of the present invention, "myocardial infarction" (heart attack, AMI (acute myocardial infarction)) shall denote an acute and life-threatening disease of the heart, wherein damage or death (infarction) of parts of the heart muscle (myocardium) occurs due to a restriction in blood supply (ischemia), which typically is present for more than 20 minutes. The cardinal symptom of a heart attack is suddenly occurring chest pain, which lasts for more than 20 minutes and is usually severe, and which can radiate into the shoulders, arms, lower jaw and upper abdomen and may be accompanied by sweating, nausea and possibly vomiting. As a result of myocardial infarction, heart failure is possible.

The term "post-myocardial infarction" means that a patient suffered from myocardial infarction in the past, which is to say, for example, more than 1 hour, in particular 20 hours, above all 1 to 5 days, or 3 to 5 days earlier, and is now living in the post phase, wherein the incident did not result in immediate death, but directly and indirectly a further disadvantageous event is to be expected, such as another (subsequent) myocardial infarction, heart failure, or death, or otherwise deterioration of the patient.

Within the context of the present invention, "cardiac insufficiency" shall also be included in "heart diseases".

"Cardiac insufficiency" is an acute or chronic inability of the heart to supply enough blood, and consequently sufficient oxygen, to the tissue in order to ensure tissue metabolism at rest or during physical activity. Clinically, cardiac insufficiency exists when typical symptoms (dyspnea, fatigue, fluid retention) are present, the underlying cause of which is a functional cardiac disorder in the sense of systolic or diastolic dysfunction. Chronic cardiac insufficiency (CCI) is also included according to the invention (Kardiologie compact, published by Chrisian Mewis, Reimer Riessen and loakim Spyridopoulos, 2nd unrevised edition, Thieme 2006). The following can be causes of cardiac insufficiency: valvular heart defect (such as a long-term consequence of rheumatic fever), myocarditis (inflammation of the heart muscle), cardiac dysrhythmias, cardiac infarction, in addition to high blood pressure (hypertension) and/or arteriosclerosis (calcification) of the coronary vessels (coronary heart disease). Also included according to the invention are hypertensive heart diseases with (congestive) heart failure, hypertensive heart and kidney disease with (congestive) heart failure, primary right heart failure, secondary right heart failure, left heart failure without discomfort (NYHA stage I), left heart failure with discomfort during higher physical activity (NYHA stage II), left heart failure with discomfort during light physical activity (NYHA stage III), left heart failure with discomfort at rest (NYHA stage IV), and cardiogenic shock.

Within the context of the present invention, "diseases of the respiratory tract and lungs" shall mean in particular "infections of the lungs and respiratory tract", specifically such infections caused by bacteria, viruses, fungi, or parasites, such as indications like lower respiratory tract infections (LRTI), bronchitis, pneumonia, sarcoidosis, bronchiectasis, or noncardiac pulmonary edema.

Additionally, according to the invention lower respiratory tract infections (LRTI), bronchitis, putrid bronchitis, and pneumonia are preferred. Particularly preferred is pneumonia, in particular community-associated pneumonia (CAP), and lower respiratory tract infections (LRTI).

Within the context of this invention, pneumonia shall be interpreted as an acute or chronic disease of the pulmonary tissue, the infection of which is caused by bacteria, viruses or fungi, parasites, rarely also toxically by the inhalation of toxic substances, or immunologically. For the clinician, pneumonia is a combination of different symptoms (fever or hypothermia, chills, coughing, pleuritic pain of the thorax, increased sputum production, increased respiratory rate, percussion sound damping, bronchial respiration, high-pitched rales, pleural friction sound), in conjunction with at least one infiltrate recognizable on the thorax x-ray image (Harrisons Innere Medizin [Harrison's Internal Medicine], published by Manfred Dietel, Norbert Suttorp and Martin Zeitz, ABW Wissenschaftsverlage 2005).

Within the context of this invention, "diseases of the respiratory tract and lungs" in particular denotes "chronic diseases of the lungs and respiratory tract", specifically such indications like interstitial lung disease and pulmonary fibrosis, chronic obstructive pulmonary disease (COPD), particularly COPD infection exacerbations, bronchial asthma, particularly infection exacerbations with bronchial asthma, and bronchial carcinoma. Particularly preferred is COPD, in particular COPD infection exacerbations.

According to the invention, COPD denotes a group of chronic diseases, which are characterized by coughing, increased expectoration, and shortness of breath during physical activity. Primarily, chronic-obstructive bronchitis and pulmonary emphysema should be mentioned. Both disease patterns are characterized in that especially expiration is labored. A colloquial term for the primary symptom of COPD is also "smoker's cough". The invention is particularly advantageous for acute exacerbations.

All indications mentioned above are also described, for example, in Pschyrembel, De Gruyter, 9th edition, Berlin 2004.

According to the invention, the term "risk stratification" comprises the identification of patients, particularly emergency patients and risk patients, having poor prognoses, for the purpose of more intensive diagnostics and therapy/treatment of heart diseases, particularly the acute coronary syndrome and myocardial infarction, angina pectoris and/or post-myocardial infarction, cardiac insufficiency, or diseases of the respiratory tract and lungs, particularly infections and chronic inflammations, with the goal of enabling the most favorable course of the disease possible. Risk stratification according to the invention consequently allows an effective treatment method, which exists for example in the case of the acute coronary syndrome in the form of percutaneous coronary interventions and newer drugs, or for the treatment or therapy of cardiac insufficiency, for example, using ACE inhibitors, AT1 antagonists, angiotensin II receptor blockers (subtype 1), the beta blockers bisoprolol, carvedilol, metoprolol and nebivolol, vasopressin receptor antagonists, aldosterone antagonists starting with NYHA stage III, calcium sensitizers (levosimendan), or for the treatment or therapy of infections or chronic diseases of the respiratory tract and lungs using antibiotics.

The invention therefore likewise relates to the identification of patients that are at increased risk and/or have an unfavorable prognosis for heart diseases and diseases of the respiratory tract and lungs, specifically symptomatic and/or asymptomatic patients, particularly emergency patients.

Particularly in cases in emergency and/or intensive care, reliable stratification can be carried out particularly advantageously by using the method according to the invention. The method according to the invention thus enables clinical decisions that result in fast success of the therapy and the prevention of fatalities. Such clinical decisions also comprise the advanced treatment with drugs for the treatment or therapy of heart diseases and diseases of the respiratory tract and the lungs.

The invention therefore also relates to a method for the diagnosis and/or risk stratification of patients with heart diseases and/or diseases of the respiratory tract and lungs for the execution of clinical decisions, such as advanced treatment and therapy using drugs, preferably in time-critical intensive or emergency care, to include the decision to hospitalize the patient.

In a further preferred embodiment, the method according to the invention therefore relates to the control of the therapy for heart diseases and/or diseases of the respiratory tract.

A further preferred embodiment, the method according to the invention for the diagnosis and/or risk stratification [is carried out] for the prognosis, early detection and detection by differential diagnosis, assessment of the severity, and assessment of the course of the disease concomitant with therapy.

In a further preferred embodiment, the invention relates to a method for in-vitro diagnostics for the early or differential diagnosis or prognosis of heart diseases and/or diseases of the respiratory tract and lungs, wherein a determination of the NT-proET-1 marker, or fragments and partial peptides thereof, is carried out in a patient to be examined.

In one embodiment of the method according to the invention, body fluid, preferably blood, optionally whole blood or serum or available plasma, is sampled from the patient to be examined, and the diagnosis is made in vitro/ex vivo, which is to say outside of the human or animal body. Due to the determination of the NT-proET-1 marker, or fragments and partial peptides thereof, a high sensitivity and specificity are achieved (refer to examples and figures), and the diagnosis or risk stratification is possible based on the available quantity in at least one patient sample.

Figure 1:
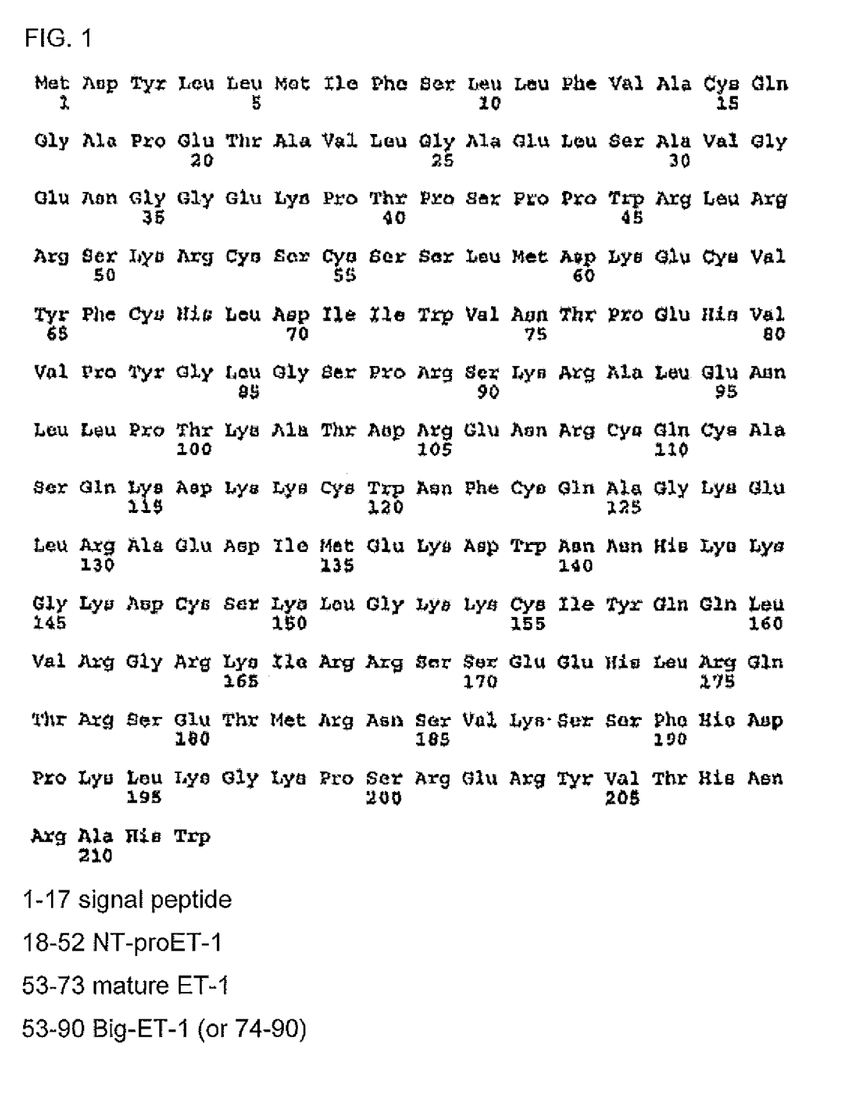
FIG. 1 shows the amino acid sequence (AS) of preproEndothelin-1 (SEQ ID NO: 1) with sections 1-17 signal peptide, 18-52 NT-proET-1, 53-73 mature ET-1, 53-90 Big-ET-1 (or 74-90).

Within the context of the present invention, "NT-proET-1" shall be interpreted as a human protein or polypeptide, which can be obtained from preproendothelin and, within the framework of preproendothelin (SEQ ID No. 1 and FIG. 1) may comprise the free fragments having amino acids 18-52 and fragments or partial peptides that can be obtained therefrom, particularly APETAVLGAELSAV (SEQ ID No. 2) Pos. 18-31 of preproET-1 (SEQ ID No. 1 and FIG. 1) and GENGGEKPTPSPPWRLRRSKR (SEQ ID No. 3) Pos. 32-52 of preproET-1 (SEQ ID No. 1 and FIG. 1). Furthermore, these polypeptides according to the invention may have posttranslational modifications, such as glycolization [sic], lipid attachment or derivatization.

In a further embodiment, the determination of NT-proET-1, or fragments and partial peptides thereof, can additionally be carried out with further markers, specifically preferably such which already point to a heart disease, particularly coronary heart disease, and/or diseases of the respiratory tract and lungs.

As a result, the invention relates to such an embodiment of the method according to the invention, wherein the determination is additionally carried out in a patient to be examined using at least one further marker selected from the group of inflammatory markers, cardiovascular markers, neurohormonal markers, or ischemic markers.

According to the invention, the inflammatory marker may be selected from at least one marker of the group of C-reactive protein (CRP), cytokines such as TNF-alpha, interleukins such as IL-6, procalcitonin (1-116, 3-116), and adhesion molecules such as VCAM or ICAM, and the cardiovascular marker may in particular be a marker indicating necrosis of the tissue of the heart muscle, and the marker influencing blood pressure can be selected from at least one marker of the group of creatine kinase, myoglobin, myeloperoxidase, natriuretic protein, particularly ANP (or ANF), proANP, NT-proANP, BNP, proBNP, NT-proBNP, or a partial sequence thereof, cardiac troponin, CRP. Furthermore, it shall also include regulatory (pro)hormones, particularly pro-gastrin releasing peptide (pro-GRP), proendothelin-2, pro-endothelin-3, pro-leptin, pro-neuropeptide Y, pro-somatostatin, pro-neuropeptide YY, pro-opionmelanocortin, pro-adrenomedullin (pro-ADM), pro-vasopressin (pro-AVP), or a partial sequence thereof. The ischemic marker may be selected from at least one marker of the group troponin I and T, CK-MB. In addition, the neurohormonal marker can be at least one further natriuretic protein, particularly ANP (or ANF), proANP, NT-proANP, BNP, proBNP, or a partial sequence thereof.

In a further embodiment of the invention, the method according to the invention can be carried out as part of an in-vitro diagnosis using parallel or simultaneous determinations of the markers (for example, multititer plates having 96 and more wells), wherein the determinations are carried out using at least one patient sample.

Furthermore, the method according to the invention and the determinations thereof can be carried out in a diagnostic device based on an automatic analysis system, particularly by means of a Kryptor (http://www.kryptor.net/).

In a further embodiment, the method according to the invention and the determinations thereof can be carried out using a rapid test (such as lateral flow test or Point of Care), be it in an individual or multiple parameter determination. In a particularly preferred embodiment, it is a self-test or a device suitable for emergency diagnostics.

The invention further relates to the use of NT-proET-1, or fragments and partial peptides thereof, for the risk stratification of heart diseases and/or diseases of the respiratory tract and lungs and/or for in-vitro diagnostics for the early or differential diagnosis or prognosis of heart diseases and/or diseases of the respiratory tract and lungs.

Another object is to provide a corresponding diagnostic device or the use thereof for carrying out the method according to the invention.

Within the context of the present invention, such a diagnostic device shall be interpreted in particular as an array or assay (such as an immunoassay, ELISA and the like), in the broadest sense a device for carrying out the method according to the invention.

The invention further relates to a kit for the diagnosis and/or risk stratification of heart diseases and/or diseases of the respiratory tract and lungs, comprising detection reagents for the determination of NT-proET-1, or fragments and partial peptides thereof, optionally above-mentioned further markers. Such detection reagents comprise antibodies and the like, for example.

The following examples and figures are provided for a more detailed description of the invention, however without limiting the invention to these examples and figures.

EXAMPLES AND FIGURES

Immunoassay

A sandwich immunoassay was used for measuring NT-proET-1 as described in Struck et al (Struck J, Morgenthaler N G, Bergmann A. Proteolytic processing pattern of the endothelin-1 precursor in vivo. Peptides 2005; 26; 2482-6).

Peptide Synthesis:

Derived from the known amino acid sequence of pre-proET-1 (FIG. 1), two areas were selected (Pos. 18-31, 32-52). The areas were chemically synthesized as soluble peptides, in one case supplemented by an N-terminal cysteine residue, using standard methods, and purified, the quality thereof was controlled using mass spectrometry and reversed-phase HPLC, and they were lyophilized in aliquots (JPT company, Berlin, Germany). The amino acid sequences of the peptides are:

PAV15 CAPETAVLGAELSAV POS. 18-31 of preproET-1 (FIG. 1) (SEQ ID NO: 4), MPGC22 GENGGEKPTPSPP-WRLRRSKRC POS. 32-52 of preproET-1 (FIG. 1) (SEQ ID NO: 5). Furthermore, a peptide comprising the area Pos. 18-52 of preproET-1 was synthesized (PAR35 APETAVL-GAELSAVGENGGEKPTPSPPWRLRRSKR (SEQ ID NO: 6)).

Conjugation and Immunization

By means of MBS (m-maleimidobenzoyl-N-hydroxysuccinimide ester), the peptides PAV15 and MPGC22 were conjugated to the KLH (keyhole limpet hemocyanin) carrier protein (see instruction sheet "NHS-Esters-Maleimide Crosslinkers" from PIERCE, Rockford, Ill., USA). These conjugates were used to immunize sheep according to the following regimen: Each sheep initially received 100 µg conjugate (quantity information relative to the peptide portion of the conjugate) and subsequently 50 µg conjugate (quantity information relative to the peptide portion of the conjugate) each in 4 week intervals. Beginning with month four after start of the immunization, 700 ml blood was collected from each sheep in 4 week intervals and from it antiserum was obtained by centrifugation. The conjugations, immunization, and production of antisera were carried out by MicroPharm, Carmarthenshire, UK.

Purification of the Antibodies

In a one-step method, the peptide-specific antibodies were produced from the antisera, which had been produced beginning with month four after immunization. For this purpose, the peptides PAV15 and MPGC22 were first coupled to SulfoLink gel (refer to instruction sheet "SulfoLink Kit" from PIERCE, Rockford, Ill., USA). For coupling, 5 mg peptide was provided per 5 ml of gel.

The affinity purification of peptide-specific antibodies from sheep antisera against the peptides was carried out as follows:

The peptide columns were first washed three times alternately using 10 ml elution buffer (50 mM citric acid, pH 2.2) and binding buffer (100 mN sodium phosphate, 0.1% Tween, pH 6.8). 100 ml of the antisera was filtered over 0.2 µm and mixed with the available column material. To this end, the gel was quantitatively rinsed out of the column with 10 ml binding puffer. The incubation was carried over night at room temperature under pivoting motion. The batches were quantitatively transferred into empty columns (NAP 25, Pharmacia, emptied). The passes were discarded. Subsequently, a washing step was carried out with 250 ml binding buffer without protein (protein content of the wash eluate <0.02 A280 nm). Elution buffer was added to the washed columns, and fractions of 1 ml each were collected. For each fraction, the protein content was determined using the BCA method (refer to instruction sheet from PIERCE, Rockford, Ill., USA). Fractions having protein concentrations of >0.8 mg/ml were pooled. After the protein determination of the pools using the BCA method, yields of 27 mg were obtained for the anti-PAV15 antibody and 35 mg for the anti-MPGC22 antibody.

Labeling

Using NAP-5 gel filtration columns (Pharmacia), 500 µl of the purified anti-MPGC22 antibody (see above) underwent a buffer exchange in 1 ml 100 mM potassium phosphate buffer (pH 8.0) according to the instruction sheet. The protein concentrations of the antibody solution were adjusted to 1.5 mg/ml using 100 mM potassium phosphate buffer (pH 8.0).

For chemiluminescence labeling, the antibody was further treated as follows: 67 µl of the antibody solution was mixed with 10 µl MA70-Akridinium-NHH-ester (1 mg/ml; HOECHST Behring) and incubated at room temperature for 15 minutes. Then 423 µl 1 M glycine was added and incubated for another 10 minutes. Subsequently, the labeling batch underwent a buffer exchange in 1 ml eluant A (50 mM potassium phosphate, 100 mM NaCl, pH 7.4) using an NAP-5 gel filtration column (Pharmacia) in accordance with the instruction sheet and in the process was freed of low-molecular components. In order to separate the remaining labels not bound to antibodies, gel filtration HPLC was carried out (column: Waters Protein Pak SW 300). The sample was applied and chromatographed at a flow rate of 1 ml/ml using eluant A. Using a photometer, the wavelengths 280 nm and 368 nm were measured. The absorption ratio of 368 nm/280 nm as a measure of the degree of labeling of the antibody was 0.10+/−0.01 at the peak. The monomer antibody-containing fractions (retention time 8-10 min) were collected and placed in 3 ml 100 mM sodium phosphate, 150 mM NaCl, 5% bovine serum albumin, 0.1% sodium azide, pH 7.4.

Coupling

Irradiated 5 ml polystyrene tubes (Greiner) was coated as follows with purified anti-PAV15 antibody: The antibody was diluted in 50 mM Tris, 100 mM NaCl, pH 7.8 to a concentration of 6.6 µg/ml. 300 µl of this solution was pipetted into each tube. The tubes were incubated for 20 hours at 22° C. The solution was suctioned. Then, each tube was filled with 4.2 ml 10 mM sodium phosphate, 2% Karion FP, 0.3% bovine serum albumin, pH 6.5. After 20 hours, the solution was suctioned. Finally, the tubes were dried in a vacuum dryer.

Execution and Evaluation of the Immunoassay

The standard material used was peptide PAR35, which was diluted serially in normal horse serum (SIGMA). The standards produced in this way were allocated to concentrations in accordance with the initial peptide weight.

The sandwich immunoassay was started as follows: 50 µl standards or samples and 200 µl assay buffer (100 mM sodium phosphate, 150 mM NaCl, 5% bovine serum albumin, 0.1% unspecific sheep IgG, 0.1% sodium azide, pH 7.4), comprising 1 million RLU (relative light units) of the MA70-labeled antibody, were pipetted in the respective test tubes coated with antibodies. The incubation was conducted for 2 hours at 22° C. while shaking. Then, 4 washing steps were carried out using 1 ml washing solution (0.1% Tween 20) each per tube, the fluid was allowed to drip off, and the chemiluminescence bound to the tube was measured using a luminometer (BERTHOLD, LB952T; base reagents BRAHMS AG). Using the MultiCalc (Spline Fit) software, the NT-proET-1 concentrations of the samples were read from the standard curve.

Analyte that can be measured using the described assay is referred to as N-terminal proendothelin-1 (NT-proET-1).

Clinical Valency

Normal Range

NT-proET-1 concentrations were determined in samples of healthy control persons (n=200). The median was 30.5 pmol/l, the smallest value measured was 2.0, the highest one was 53 pmol/l, the 95th percentiles were 16.3 and 47.2 pmol/l.

Cardiac Insufficiency/Severity

Figure 2:
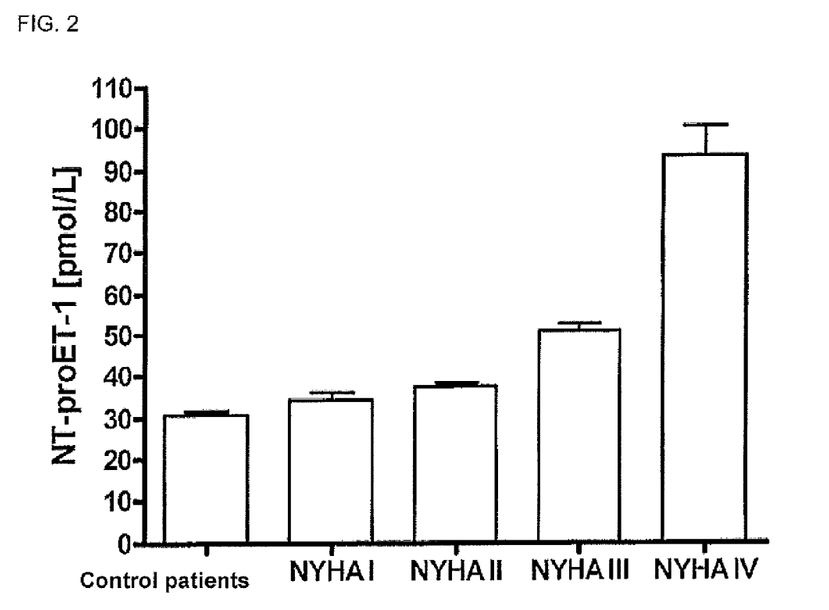

NT-proET-1 concentrations were measured for patients with chronic or acute decompensated cardiac insufficiency. NT-proET-1 concentrations were associated with the severity of the cardiac insufficiency, particularly with increased severity: The medians of NT-proET-1 concentrations for the four severity categories NYHA I-IV were: 35.4, 37.3, 45.5 and 83.9 pmol/L (refer to FIG. 2).

Chronic Cardiac Insufficiency/Diagnosis

NT-proET-1 values were determined from a pool of 316 patients suffering from chronic cardiac insufficiency and 200 healthy control patients. The receiver-operating characteristic analysis showed an AUC of 0.72. For a cut-off value of 49.7 pmol/l, this produced a sensitivity of 34.3% with a specificity of 98%. For a cut-off value of 47.2 pmol/l, this produced a sensitivity of 38.5% with a specificity of 95%.

Chronic Cardiac Insufficiency/Prognosis

NT-proET-1 values were determined from a pool of 316 patients suffering from chronic cardiac insufficiency. The patients were monitored for a mean period of 360 days. During this period, 42 patients passed away, 274 survived. Using the receiver-operating characteristic analysis, the best cut-off value (defined as the largest product of sensitivity and specificity) was determined for the prognosis of the mortality rate: 51.3 pmol/l. At this cut-off value, the sensitivity of the prognosis was 71.4%, the specificity was 74.5%. The likelihood ratio of passing away at a cut-off value of 51.3 pmol/l was 2.8.

|  | <51.3 pmol/l | >51.3 pmol/l |
|---|---|---|
| Survivors | 204 | 70 |
| Fatalities | 12 | 30 |

Acute Cardiac Insufficiency/Diagnosis

NT-proET-1 values were determined from a pool of 125 patients suffering from acute shortness of breath. 69 of the 125 patients suffered from cardiac insufficiency. The receiver operating characteristic analysis for the differential diagnosis of cardiac insufficiency showed an AUC of 0.72. For a cut-off value of 111 pmol/l, this produced a sensitivity of 10.2% with a specificity of 98%. For a cut-off value of 90.5 pmol/l, this produced a sensitivity of 17.5% with a specificity of 95%.

Acute Cardiac Insufficiency/Prognosis

NT-proET-1 values were determined from a pool of 69 patients suffering from acute decompensated cardiac insufficiency. The patients were monitored for a period of 360 days.

During this period, 21 patients passed away, 48 survived. Using the receiver-operating characteristic analysis, the best cut-off value (defined as the largest product of sensitivity and specificity) was determined for the prognosis of the mortality rate: 64 pmol/l. At this cut-off value, the sensitivity of the prognosis was 66.6%, the specificity was 68.7%. The likelihood ratio of passing away at a cut-off value of 64 pmol/l was 2.0.

|  | <64 pmol/l | >64 pmol/l |
|---|---|---|
| Survivors | 33 | 15 |
| Fatalities | 7 | 14 |

Myocardial Infarction/Prognosis

Samples were obtained from 246 patients with acute heart attacks three days after the heart attack occurred, and NT-proET-1 was measured. The patients were monitored for a period of 60 days. During this period, 220 patients had no adverse event, 26 passed away or were hospitalized again due to cardiac insufficiency. Using the receiver-operating characteristic analysis (AUC=0.70), the best cut-off value (defined as the largest product of sensitivity and specificity) was determined for the prognosis of the mortality rate or rehospitalization due to cardiac insufficiency: 63.9 pmol/l. At this cut-off value, the sensitivity of the prognosis was 65.4%, the specificity was 73.6%. The likelihood ratio of an adverse event at a cut-off value of 63.9 pmol/l was 2.5.

|  | <63.9 pmol/l | >63.9 pmol/l |
|---|---|---|
| No adverse event | 162 | 58 |
| Fatalities/cardiac insufficiency | 9 | 17 |

Pneumonia/Severity and Prognosis

Figure 3:
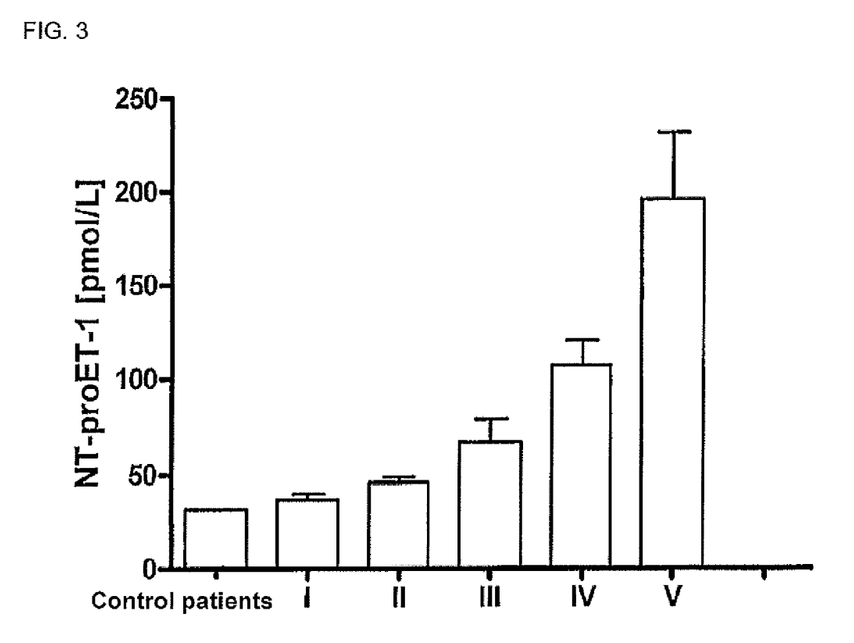
FIG. 3: NT-proET-1 concentrations as a function of the severity of pneumonia. Illustrated are the mean values (+SEM) of healthy control patients (n=200) and of pneumonia patients grouped based on the Pneumonia Severity Index (PSI I: n=36, PSI II: n=44, PSI III: n=25, PSI IV: n=19, PSI V: n=18).

Samples were obtained from 142 patients with community-associated pneumonia upon admission to the hospital, and NT-proET-1 was measured. The patients were monitored for a period of 70 days. During this period, 10 patients passed away. NT-proET-1 concentrations rose with the PSI (pneumonia severity index), a score of the severity of the disease (FIG. 3), and at 53 pmol/l they were on average higher than in the healthy control patients (30.5 pmol/l). For the prognosis of mortality, the receiver-operating characteristic analysis showed an AUC of 0.89. Using the receiver-operating characteristic analysis, the best cut-off value (defined as the largest product of sensitivity and specificity) was determined for the prognosis of the mortality rate: 77 pmol/l. At this cut-off value, the sensitivity of the prognosis was 100%, the specificity was 81.2%. The likelihood ratio of mortality at a cut-off value of 77 pmol/l was 5.5.

|  | <77 pmol/l | >77 pmol/l |
|---|---|---|
| No adverse event | 108 | 24 |
| Fatalities | 0 | 10 |

Exacerbated COPD

NT-proET-1 was measured for 53 patients with chronic obstructive pulmonary disease and simultaneous infection of the lower respiratory tract. With a mean of 47 pmol/l, these patients had higher values compared to the healthy control patients (30.5 pmol/l), however lower than the pneumonia patients (see above 53 pmol/l).

TABLE

| Classification of the New York Heart Association (NHYA) | |
|---|---|
| NYHA I | No limitation of physical activity. Ordinary physical activity does not cause undue fatigue, dysrhythmia, dyspnea or angina pectoris. |
| NYHA II | Slight limitation of physical activity. Comfortable at rest, but ordinary physical activity results in fatigue, dysrhythmia, dyspnea or angina pectoris. |
| NYHA III | Marked limitation of physical activity. Comfortable at rest, but less than ordinary physical activity causes fatigue, dysrhythmia, dyspnea or angina pectoris. |
| NYHA IV | Unable to carry out any physical activity without discomfort and discomfort at rest. Bedridden. |

DESCRIPTION OF THE FIGURES

FIG. 2:

NT-proET-1 concentrations as a function of the severity of cardiac insufficiency. Illustrated are the mean values (+SEM) of healthy control patients (n=200) and of cardiac insufficiency patients grouped based on the NYHA severity score (NYHA I: n=22, NYHA II: n=126, NYHA III: n=132, NYHA 4: n=17).

The invention claimed is:

1. A method for the in-vitro diagnosis and/or risk stratification of heart diseases and/or diseases of the lungs and respiratory tract selected from the group consisting of cardiac insufficiency, post myocardial infarction, pneumonia and exacerbated chronic obstructive pulmonary disease comprising (a) contacting at least one sample of bodily fluid from a patient with an antibody specific for the polypeptide consisting of the amino acid sequence APETAVL-GAELSAVGENGGEKPTPSPPWRLRRSKR (SEQ ID NO: 6), known as NT-proET-1, (b) detecting binding of said antibody to NT-proET-1 using an immunoassay to determine the level of NT-proET-1 in said at least one sample, and (c) diagnosing the presence or stratifying the risk of heart diseases and/or diseases of the lungs and respiratory tract in the patient based on the result in steps (a) and (b), wherein the presence of a higher level of NT-proET-1 in said at least one sample compared to healthy controls indicates the presence of a heart disease or disease of the lungs and respiratory tract in said patient, or an increased risk of an unfavorable prognosis for heart disease or disease of the lungs and respiratory tract and wherein said heart disease or disease of the lungs and respiratory tract are selected from the group consisting of cardiac insufficiency, post myocardial infarction, pneumonia and exacerbated chronic obstructive pulmonary disease.

2. A method according to claim 1, characterized in that additionally a determination of at least one further marker is carried out, selected from the group of inflammatory markers, cardiovascular markers, neurohormonal markers, or ischemic markers.

3. A method according to claim 2, characterized in that the inflammatory marker is selected from at least one marker of the group of C-reactive protein (CRP), cytokines such as TNF-alpha, interleukines such as IL-6, procalcitonin (1-116, 3-116), and adhesion molecules such as VCAM or ICAM.

4. A method according to claim 2, characterized in that the cardiovascular marker is selected from at least one marker of the group creatine kinase, myoglobin, myeloperoxidase, natriuretic protein, particularly ANP (or ANF), proANP, NT-proANP, BNP, proBNP, NT-proBNP, or a partial sequence thereof, cardiac troponin, CRP, and also regulatory (pro)hormones, such as pro-gastrin releasing peptide (pro-GRP), pro-endothelin-2, pro-endothelin-3, pro-leptin, pro-neuropeptide Y, pro-somatostatin, pro-neuropeptide YY, pro-opionmelanocortin, pro-adrenomedullin (pro-ADM), pro-vasopressin (pro-AVP), or a partial sequence thereof.

5. A method according claim 2, characterized in that the ischemic marker is selected from at least one marker of the group troponin I and T, CK-MK.

6. A method according to claim 2, characterized in that the neurohormonal marker is at least one natriuretic protein, particularly ANP (or ANF), proANP, NT-proANP, BNP, proBNP, NT-proBNP, or a partial sequence thereof.

7. A method according to claim 2, characterized in that parallel or simultaneous determinations of the markers are carried out.

8. A method according to claim 1, characterized in that the determinations are carried out using an automatic analysis system, particularly by means of a Kryptor.

9. A method according to claim 1, characterized in that the determinations are carried out using a rapid test, particularly in individual or multiple parameter determinations.

10. The method of claim 1 wherein said antibody specific for NT-proET-1 binds to the area of NT-proET-1 comprised of SEQ ID NO: 2 or binds to the area of NT-proET-1 comprised of SEQ ID NO: 3.

11. The method of claim 10 wherein said antibody specific for NT-proET 1 binds to SEQ ID NO: 4, or said antibody specific for NT-proET-1 binds to SEQ ID NO: 5.

12. The method of claim 1, wherein said heart disease is cardiac insufficiency, and wherein the presence of a higher level of NT-pro-ET1, with a cut off value of 47.2 pmol/ml, in said at least one sample compared to healthy controls indicates the presence of chronic cardiac insufficiency in said patient.

13. The method of claim 1, wherein said heart disease is chronic cardiac insufficiency, and wherein the presence of more than 51.3 pmol/ml of NT-pro-ET1 in said at least one sample indicates an increased likelihood of death of said patient.

14. The method of claim 1, wherein said heart disease is cardiac insufficiency, and wherein the presence of a higher level of NT-pro-ET1, with a cut off value of 90.5 pmol/ml, in said at least one sample compared to healthy controls indicates the presence of acute cardiac insufficiency in said patient.

15. The method of claim 1, wherein said heart disease is acute cardiac insufficiency, and wherein the presence of more than 64 pmol/ml of NT-pro-ET1 in said at least one sample indicates an increased likelihood of death of said patient.

16. The method of claim 1, wherein said heart disease is post-myocardial infarction, and wherein the presence of more than 63.9 pmol/ml of NT-pro-ET1 in said at least one sample indicates an increased likelihood of rehospitalization of said patient due to cardiac insufficiency or death of said patient.

17. The method of claim 1, wherein said disease of the lungs and respiratory tract is pheumonia, and wherein the presence of more than 77 pmol/ml of NT-pro-ET1 in said at least one sample indicates an increased likelihood of death of said patient.

18. The method of claim 1, wherein said disease of the lungs and respiratory tract is exacerbated chronic obstructive pulmonary disease, and wherein the presence of a level of NT-proET-1 greater than 30.5 pmol/ml but less than 53 pmol/ml in said at least one sample indicates the presence of exacerbated chronic obstructive pulmonary disease in said patient.

* * * * *

SEQUENCE LISTING

```
<160> NUMBER OF SEQ ID NOS: 6

<210> SEQ ID NO 1
<211> LENGTH: 212
<212> TYPE: PRT
<213> ORGANISM: Homo sapiens

<400> SEQUENCE: 1

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30
```

-continued

Glu Asn Gly Gly Glu Lys Pro Thr Pro Ser Pro Pro Trp Arg Leu Arg
            35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
            115                 120                 125

Leu Arg Ala Glu Asp Ile Met Glu Lys Asp Trp Asn Asn His Lys Lys
            130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu His Leu Arg Gln
                165                 170                 175

Thr Arg Ser Glu Thr Met Arg Asn Ser Val Lys Ser Phe His Asp
            180                 185                 190

Pro Lys Leu Lys Gly Lys Pro Ser Arg Glu Arg Tyr Val Thr His Asn
            195                 200                 205

Arg Ala His Trp
    210

<210> SEQ ID NO 2
<211> LENGTH: 14
<212> TYPE: PRT
<213> ORGANISM: Homo sapiens

<400> SEQUENCE: 2

Ala Pro Glu Thr Ala Val Leu Gly Ala Glu Leu Ser Ala Val
1               5                   10

<210> SEQ ID NO 3
<211> LENGTH: 21
<212> TYPE: PRT
<213> ORGANISM: Homo sapiens

<400> SEQUENCE: 3

Gly Glu Asn Gly Gly Glu Lys Pro Thr Pro Ser Pro Pro Trp Arg Leu
1               5                   10                  15

Arg Arg Ser Lys Arg
            20

<210> SEQ ID NO 4
<211> LENGTH: 15
<212> TYPE: PRT
<213> ORGANISM: Artificial
<220> FEATURE:
<223> OTHER INFORMATION: synthetic peptide

<400> SEQUENCE: 4

Cys Ala Pro Glu Thr Ala Val Leu Gly Ala Glu Leu Ser Ala Val
1               5                   10                  15

<210> SEQ ID NO 5
<211> LENGTH: 22
<212> TYPE: PRT

```
<213> ORGANISM: artificial
<220> FEATURE:
<223> OTHER INFORMATION: synthetic peptide

<400> SEQUENCE: 5

Gly Glu Asn Gly Gly Glu Lys Pro Thr Pro Ser Pro Pro Trp Arg Leu
1               5                   10                  15

Arg Arg Ser Lys Arg Cys
            20

<210> SEQ ID NO 6
<211> LENGTH: 35
<212> TYPE: PRT
<213> ORGANISM: Homo sapiens

<400> SEQUENCE: 6

Ala Pro Glu Thr Ala Val Leu Gly Ala Glu Leu Ser Ala Val Gly Glu
1               5                   10                  15

Asn Gly Gly Glu Lys Pro Thr Pro Ser Pro Pro Trp Arg Leu Arg Arg
            20                  25                  30

Ser Lys Arg
        35
```